United States Patent [19]

Richards et al.

[11] Patent Number: 5,024,518
[45] Date of Patent: Jun. 18, 1991

[54] OPHTHALMIC CONTACT LENS WITH INTERNAL FIXATION LIGHT FOR EXAMINATION OF THE OPTIC NERVE

[75] Inventors: David W. Richards, Tampa, Fla.; Kent A. Murphy, Roanoke, Va.

[73] Assignees: Center for Innovative Technology, Herndon; Virginia Commonwealth University, Richmond; Virginia Polytechnic Institute and State University, Blacksburg, all of Va.

[21] Appl. No.: 497,596

[22] Filed: Mar. 22, 1990

[51] Int. Cl.$^5$ ............................................. A61B 3/00
[52] U.S. Cl. .................................... 351/219; 351/221
[58] Field of Search ................ 351/219, 221, 208, 205

[56] References Cited

U.S. PATENT DOCUMENTS

| | | |
|---|---|---|
| 3,439,978 | 4/1969 | Moore et al. . |
| 3,589,800 | 6/1971 | Cardona . |
| 3,630,602 | 12/1971 | Herbert . |
| 3,780,979 | 12/1973 | deGuillebon . |
| 3,944,341 | 3/1976 | Pomerantzeff . |
| 3,954,329 | 5/1976 | Pomerantzeff . |
| 4,007,980 | 2/1977 | Bracher et al. . |
| 4,056,310 | 11/1977 | Shimizu et al. . |
| 4,169,664 | 10/1979 | Bailey . |
| 4,485,820 | 12/1984 | Flower . |
| 4,553,824 | 11/1985 | Abe . |
| 4,573,778 | 3/1986 | Shapiro . |
| 4,871,247 | 10/1989 | Haynes . |

FOREIGN PATENT DOCUMENTS 3228243  7/1982  Fed. Rep. of Germany .

Primary Examiner—Paul M. Dzierzynski
Attorney, Agent, or Firm—Whitham & Marhoefer

[57] ABSTRACT

An instrument and method for examining the optic nerve head (34) of a patient's eye (14) is disclosed. The instrument is comprised of a gonioscopic lens (10) a lens system (26) where the lens system (26) directs a collimated beam of light towards a point (32) away from the center line (28) through the gonioscopic lens (10) and eye (14). When the patient fixates on the beam of light (32), the ophthalmologist can examine the optic nerve head (34) through the gonioscopic lens (10).

8 Claims, 2 Drawing Sheets

$$l_2 = \frac{1}{n_0\sqrt{A}} \cdot \frac{n_0\sqrt{A} l_1 \cos(\sqrt{A}Z) + \sin(\sqrt{A}Z)}{n_0\sqrt{A} l_1 \sin(\sqrt{A}Z) - \cos(\sqrt{A}Z)}$$

$$n(r) = n_0\left(1 - \frac{A}{2}r^2\right)$$

OPHTHALMIC CONTACT LENS WITH INTERNAL FIXATION LIGHT FOR EXAMINATION OF THE OPTIC NERVE

BACKGROUND OF THE INVENTION

1. Field of the Invention

The present invention is generally related to eye examining instrumentation and, more particularly, to a hand held instrument used for inspecting the optic nerve of a patient's eye.

2. Description of the Prior Art

Glaucoma is a disease of the eye which causes partial or complete loss of sight. Glaucoma is characteristically accompanied by hardening of the eyeball, increased intraocular pressure, and damage to the optic nerve. Proper diagnosis of glaucoma should include measurement of the intraocular pressure, study of visual field tests, and an examination of the optic nerve. The treatment of glaucoma requires relieving pressure in the eye; this is typically done by the use of drugs, lasers or surgery, all of which entail risks to the patient. It would therefore not be sound practice to prescribe such treatment for glaucoma if the optic nerve was undamaged. Patients may, for example, have a high pressure condition in the eye with no damage to the optic nerve. This condition is called ocular hypertension. Hence, careful examination of the optic nerve should be performed before any treatment is given.

In order to examine the optic nerve, a patient must be looking in a direction which allows the ophthalmologist to analyze the optic nerve head (which is located in the plane of the retina). Currently, a patient is asked to look at objects in the ophthalmologist's office or at a light positioned to one side of the patient's head. In this technique, the patient's free eye is used to fixate on the object and the optic nerve head in the patient's eye under examination becomes exposed because it follows the free eye. This is a time consuming process since it is difficult for the patient to fixate on a particular object when an examining lens is pressed against one of the patient's eyes. In addition, fixation by this technique in functionally monocular patients is not possible because they do not have a fellow eye with which they can look at the object. This situation is often aggravated in glaucoma patients by a constricted and fixed pupil.

SUMMARY OF THE INVENTION

It is therefore an object of the present invention to provide a fundoscopic contact lens which incorporates a fixation target that allows the patient to view the target with the eye being examined.

According to the invention, a fixation target has been incorporated into a corneal contact lens. The fixation target is a collimated beam of light which is directed towards a particular location (the fovea) in the eye that is offset from the optic nerve head. With the contact lens in place, the patient is asked to view the target with the eye being examined. Since the fovea is the location of greatest visual acuity, it will automatically move into alignment with the target beam. The optic nerve head of the eye then comes into the ophthalmologist's view through the contact lens.

BRIEF DESCRIPTION OF THE DRAWINGS

The foregoing and other objects, aspects and advantages will be better understood from the following detailed description of the preferred embodiment of the invention with reference to the drawings, in which.

DETAILED DESCRIPTION OF A PREFERRED EMBODIMENT OF THE INVENTION

Figure 1:
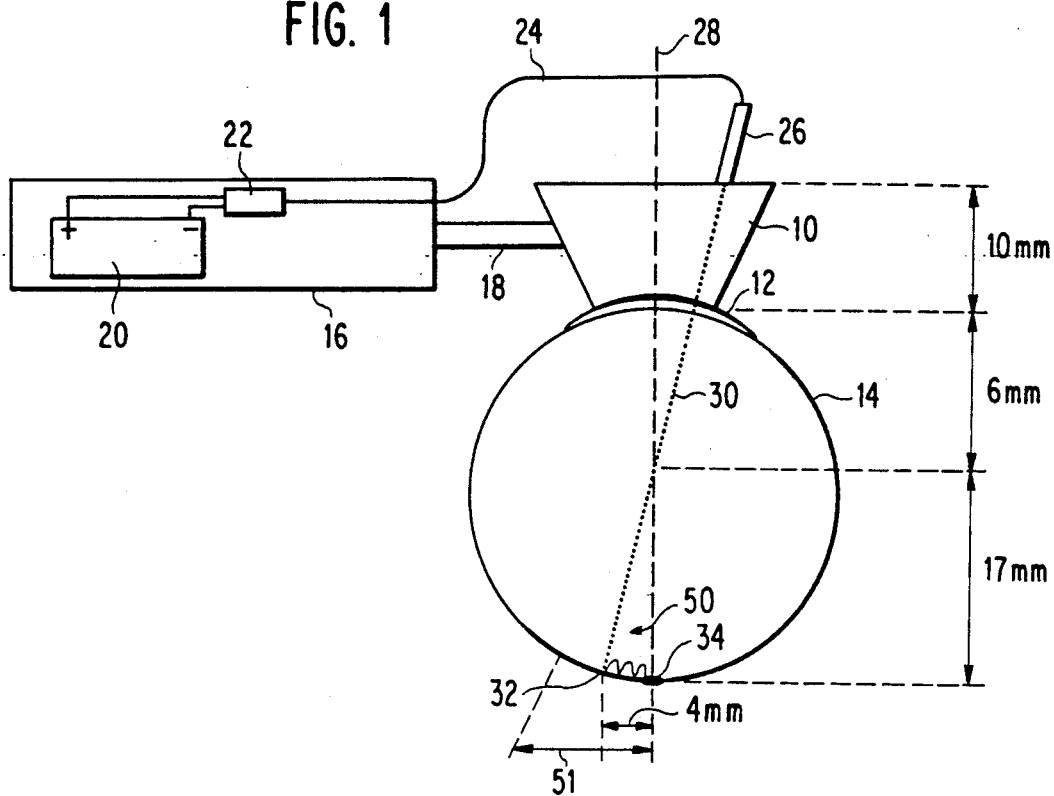
FIG. 1 is a representational side view of a hand held optic nerve examining instrument in contact with an eyeball showing schematically the electrical and optic elements of the invention.

Referring now to the drawings, and more particularly to FIG. 1, there is shown a gonioscopic contact lens 10 positioned on the cornea 12 of a patients left eye 14 as viewed from above. Gonioscopic contact lenses 10 are available from the Zeiss company of Germany. The gonioscopic contact lens 10 is supported by a handle 16 and supporting bar 18 arrangement. A battery pack 20 which is electrically connected to light emitting diode (LED) 22 is located within the handle 16. Light from LED 22 is transported by optical fiber 24 to a lens system 26 mounted on the gonioscopic lens 10. The lens system 26 is mounted at a position offset from the center line 28 through the gonioscopic lens 10 and directs a collimated beam of light 30 towards a position 32 (the fovea), offset from the center line 28.

Lens systems 26 for producing collimated beams of light 30 are well known in the art. The key feature required by this invention is that the beam of light 30 be offset from center 28. The offset angle 50 in the normal eye is approximately fifteen degrees (15°).

A patient's eye will normally be able to detect the beam by looking slightly in the nasal direction, permitting the light beam 30 to fall on the macula 51. The macula 51 is a disk shaped area of especially light sensitive retina which surrounds the fovea. The fovea is the point of greatest sensitivity of the retina. The angular radius of the macula is approximately 15°. In operation, once the light beam 30 is detected by the macula 5I, the eye 14 normally will rapidly achieve more exact alignment to the fovea. When the fovea of the eye 14 moves to position 32, the optic nerve head 34 is observable by the ophthalmologist through the gonioscopic lens 10.

In operation, the ophthalmologist places the gonioscopic lens 10 on the patients cornea 12 with his hand (not shown) located temporally relative to the eye 14 and the lens system 26 located nasally relative to the eye 14. A switch (not shown) is used to turn LED 22 on so that the collimated beam of light 30 is directed into the eye 14. The patient is asked to focus on the beam of light 30. When the fovea of the eye 14 lines up with the beam of light 30, the ophthalmologist observes the optic nerve head 34 and diagnoses whether any damage has occurred. Having the patient focus on a target, i.e., light beam 30, with the eye 14 under examination is believed to allow two eyed patients to fixate properly within a shorter period of time and to provide one eyed patients with a means to fixate (something they were unable to do in the past).

Figure 2:
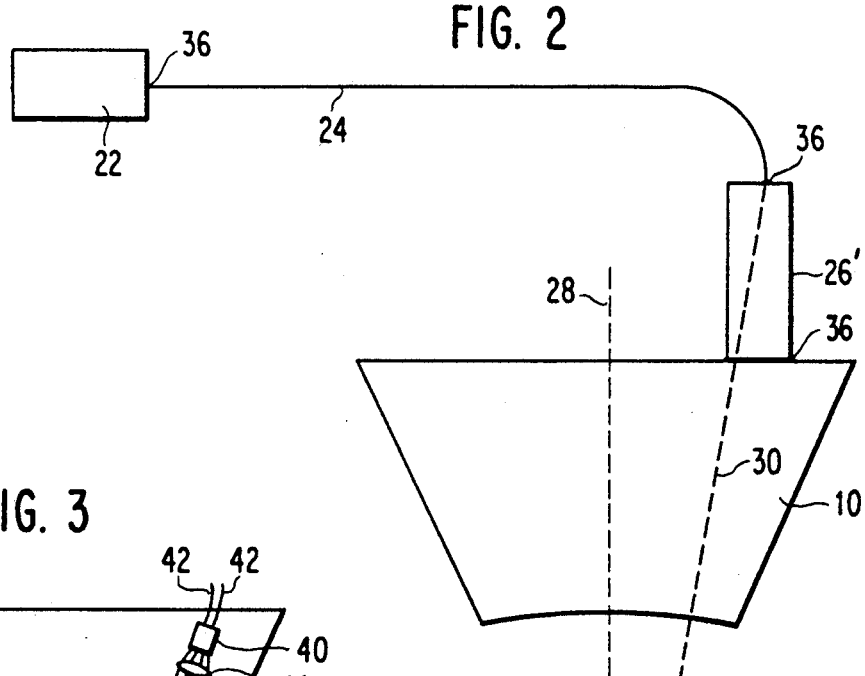
FIG. 2 is a representational side view of a contact lens with a graded index (GRIN) lens mounted thereon in a position offset from center.

FIG. 2 shows a preferred embodiment of the present invention wherein a GRIN lens 26' is affixed to the gonioscopic lens 10 using an epoxy compound 36. GRIN lenses are available from NSG America of Somerset, N.J. and are sold under the trade name SELFOC. GRIN lenses have the inherent property of collimating a beam of light 30 and steering it in a particular direction. An advantage of the GRIN lens 26' is that it can be affixed normally to the top plane of gonioscopic lens 10; thereby, eliminating machining and alignment problems encountered with other lens systems 26. The optical fiber 24 has polished end faces which are held to the LED 22 and the GRIN lens 26 by epoxy 36.

Figure 4:
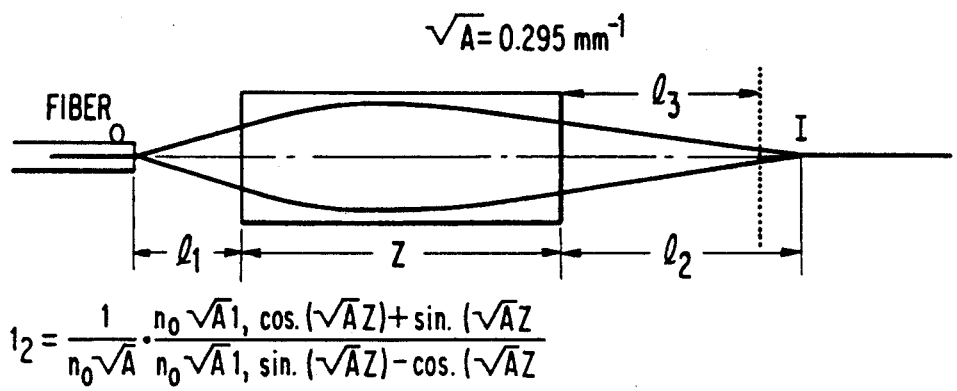
FIG. 4 is a schematic diagram and equation used to calculate the length of a GRIN lens for use on the instrument shown in FIG. 2.
Figure 5:
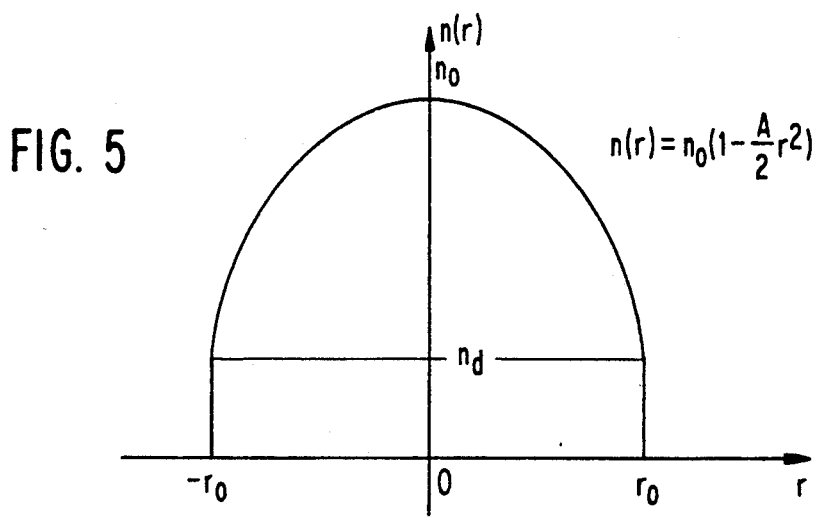
FIG. 5 is a graphical representation and equation describing the refractive index profile of a GRIN lens.

In order for the collimated beam of light 30 to be directed to point 32 in the eye 14, the designer must consider the height and diameter of the GRIN lens 26', the refractive indexes of the GRIN lens 26', the gonioscopic lens 10, and the epoxy compound 36, and the position on top of the GRIN lens 26' where the optical fiber 24 is connected. FIG. 4 shows an equation used to estimate the length Z of the GRIN or SELFOC lens 26' shown in FIG. 2 required once the working distances are known. FIG. 5 shows a graphical representation and an equation describing the refractive index profile of the GRIN or SELFOC lens 26'. Referring back to FIG. 1, the working distances for use of the instrument on a normal eye 14 are provided. In FIG. 1, the light beam 30 passes through a 10 millimeter (mm) gonioscopic lens 10 then travels through approximately 23 mm of the eye 14 where the light beam 30 crosses over center line 28 at a point 6 mm from the surface of the eye 14 and travels another 17 mm to point 32 located 4 mm from center line 28. From these calculations, it has been determined that the length of GRIN lens 26' is approximately 2.0 mm, which makes it approximately a 0.12 pitch lens. This configuration gives a cone of light about five to ten degrees.

Figure 6:
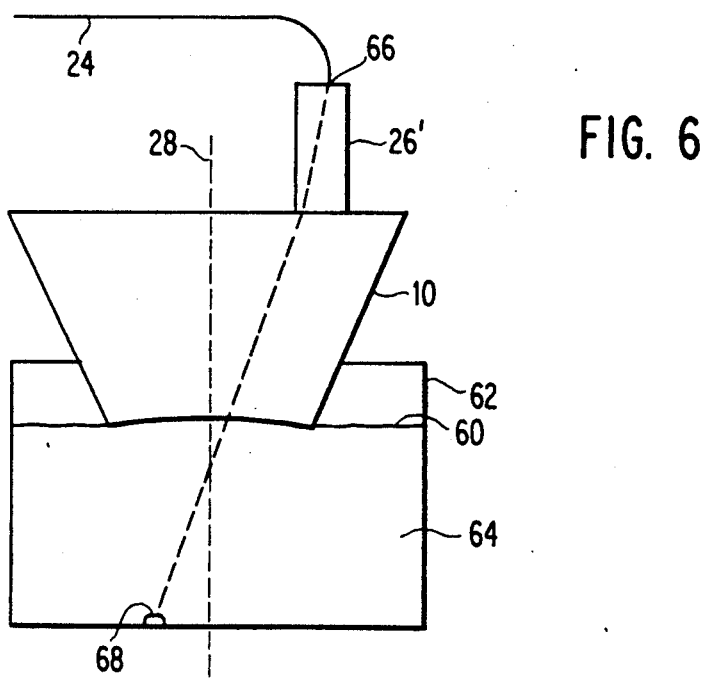
FIG. 6 is a representational side view of the lens arrangement shown in FIG. 2 where an alignment procedure is performed using water as a medium.

FIG. 6 shows the experimental set up used to align the fiber 24 with the GRIN lens 26'. The gonioscopic lens 10 is placed at the water line 60 in a beaker 62 of water 64. Water 64 is used to simulate the eye 14 because it has a similar index of refraction. A five axis positioner (not shown) is then used to align the fiber 24 to the GRIN lens 26'. In operation, the fiber 24 is moved to a position 66 that projects a spot 68, of the desired size and offset position, and then the fiber 24 is glued into place using epoxy or any other suitable compound.

Figure 3:
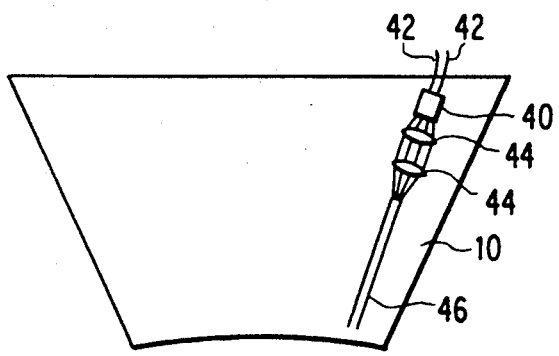
FIG. 3 is a representational side view of a contact lens with a fixation target embedded therein at a position offset from center.

FIG. 3 shows an alternative arrangement for the present invention wherein an LED 40 is embedded within the gonioscopic lens 10. Electrical leads 42 connect the LED 40 to a battery pack (not shown). Light from the LED 40 is collimated by lenses 44 and directed through fiber optic bundle 46 towards point 32 (shown in FIG. 1) in the eye.

While the invention has been described in terms of its preferred embodiment wherein a target light source for fixating the patient's line of sight is provided with the lens of the optic nerve analyzing instrument, those skilled in the art will recognize that the invention can be practiced with modification within the spirit and scope of the appended claims.

Having thus described our invention, what we claim as new and desire to secure by Letters Patent is as follows:

1. An instrument for examining the optic nerve in a patient's eye, comprising:
   a contact lens for placement on the cornea of said patient's eye;
   a source of light for providing a fixation target in said contact lens for said patient's eye;
   a means for collimating and directing a narrow diameter beam of light from said source of light to a point in said patient's eye a fixed distance away from the optic nerve head of said patient's eye; and
   a means for observing the optic nerve of said patient's eye.

2. An instrument as recited in claim 1 wherein said source of light comprises a light emtiting diode connected to said means for collimating and directing said narrow diameter beam of light by an optical fiber.

3. An instrument as recited in claim 1 wherein said means for collimating and directing said narrow diameter beam of light includes a graded index lens, said graded index lens being mounted on said contact lens at a position offset from a center line through said contact lens.

4. An instrument as recited in claim 1 wherein said source of light is a light emitting diode and said means for collimating and directing said narrow diameter beam of light includes a lens system, both said light emitting diode and said lens system being embedded in said contact lens.

5. An instrument as recited in claim 1 wherein said contact lens is a gonioscopic lens.

6. An instrument for examining the optic nerve in a patient's eye, comprising:
   a contact lens for placement on the cornea of said patient's eye;
   a graded index lens mounted on said contact lens at a position offset from a center line through said contact lens;
   a source of light connected to said graded index lens by an optical fiber, said graded index lens directing a narrow diameter beam of light to a point in said patient's eye a fixed distance away from the optic nerve head of said patient's eye.

7. An instrument for examining the optic nerve of a patient's eye, comprising:
   a contact lens for placement on the cornea of said patient's eye;
   a light source embedded in said contact lens at a position offset from a center line through said contact lens;
   a means for collimating and directing a narrow diameter beam of light from said light source to a point in said patient's eye a fixed distance away from the optic nerve head of said patient's eye; and
   a means for observing the optic nerve of said patient's eye.

8. A method for examining the optic nerve in a patient's eye, comprising the step of:
   placing a contact lens on the cornea of said patient's eye;
   directing a narrow diameter, a collimated beam of light through said contact lens to a point in said patient's eye a fixed distance away from the optic nerve head of said patient's eye; and
   observing the optic nerve through said contact lens while said patient's eye is fixated on said narrow diameter, collimated beam of light.

* * * * *